(12) United States Patent
Phan et al.

(10) Patent No.: US 6,299,440 B1
(45) Date of Patent: Oct. 9, 2001

(54) SYSTEM AND METHOD FOR PRODUCING TOOTH MOVEMENT

(75) Inventors: Loc X. Phan, San Francisco; Muhammad Chishti, Sunnyvale, both of CA (US)

(73) Assignee: Align Technology, INC, Santa Clara, CA (US)

(*) Notice: Subject to any disclaimer, the term of this patent is extended or adjusted under 35 U.S.C. 154(b) by 0 days.

(21) Appl. No.: 09/483,071

(22) Filed: Jan. 14, 2000

Related U.S. Application Data

(60) Provisional application No. 60/116,007, filed on Jan. 15, 1999.

(51) Int. Cl.[7] .................... A61C 3/00; A61C 5/00
(52) U.S. Cl. .................... 433/24; 433/6; 433/215; 433/18
(58) Field of Search .................... 433/6, 18, 24, 433/215

(56) References Cited

U.S. PATENT DOCUMENTS

| | | |
|---|---|---|
| 3,600,808 | 8/1971 | Reeve . |
| 3,683,502 | 8/1972 | Wallshein . |
| 3,984,915 | 10/1976 | Noble et al. . |
| 4,153,060 | 5/1979 | Korostoff et al. . |
| 4,253,828 | 3/1981 | Coles et al. . |
| 4,664,626 | 5/1987 | Kesling . |
| 4,676,747 | 6/1987 | Kesling . |
| 4,850,865 | 7/1989 | Napolitano . |
| 4,877,398 | 10/1989 | Kesling . |
| 5,055,039 | * 10/1991 | Abbatte et al. .................... 433/24 |
| 5,059,118 | * 10/1991 | Breads et al. .................... 433/24 X |
| 5,125,832 | 6/1992 | Kessling . |
| 5,975,893 | 11/1999 | Chishti et al. . |
| 6,183,248 | * 2/2001 | Chisti et al. .................... 433/24 X |

FOREIGN PATENT DOCUMENTS

WO 98/58596 12/1998 (WO) .

* cited by examiner

*Primary Examiner*—Nicholas D. Lucchesi
(74) *Attorney, Agent, or Firm*—Townsend and Townsend and Crew LLP

(57) ABSTRACT

The present invention provides methods and systems of repositioning teeth for use in orthodontic treatment, with particular applicability to removable elastic repositioning appliances. Such appliances may be challenged by traditional tooth movements which intrude the crown of the tooth or present tooth positions which reduce available points of purchase. These challenges may be overcome with a series of tooth movements in which a tooth is translated in a "root-first" position. The movements may take advantage of the inherent characteristics of elastic repositioning appliances in translating a tooth from a first position to a desired position along a gingival plane.

15 Claims, 12 Drawing Sheets

FIG. 5A START

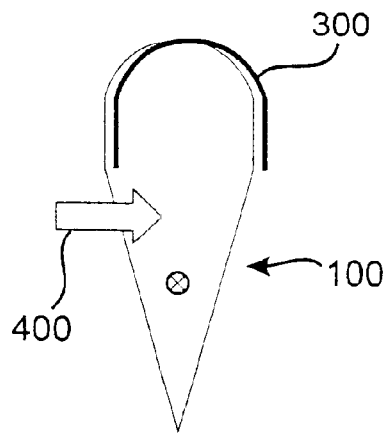 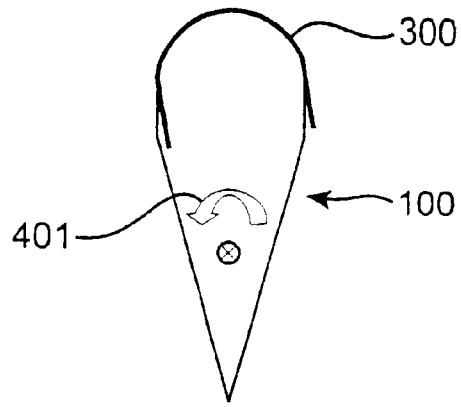
FIG. 10A  FIG. 10B
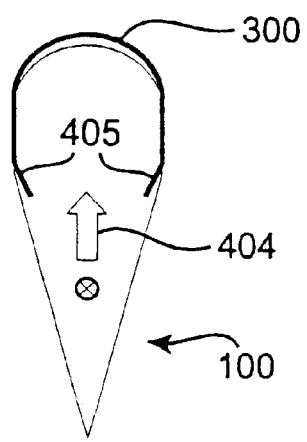 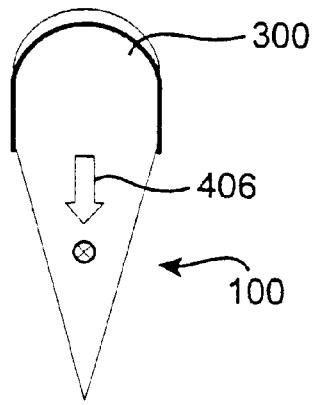
FIG. 10C  FIG. 10D

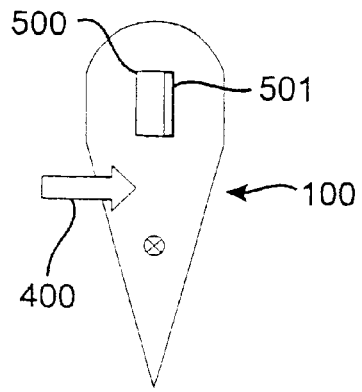
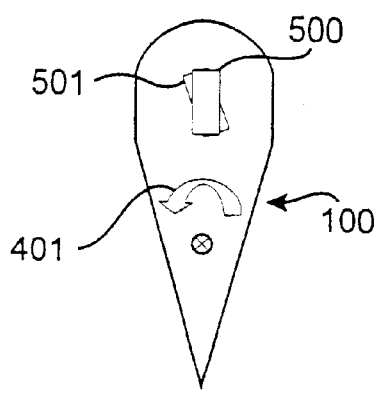
FIG. 12A     FIG. 12B
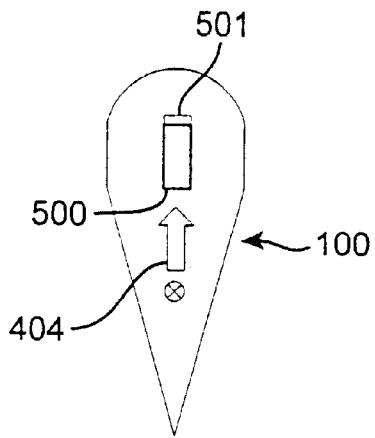
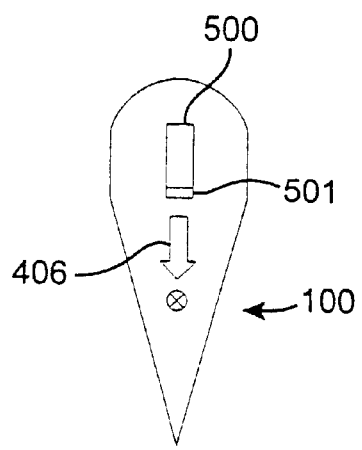
FIG. 12C     FIG. 12D
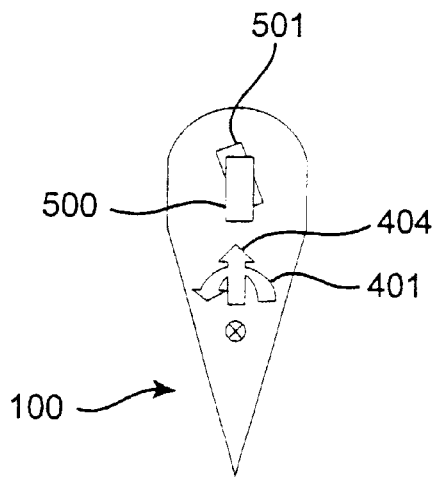
FIG. 13

SYSTEM AND METHOD FOR PRODUCING TOOTH MOVEMENT

CROSS-REFERENCES TO RELATED APPLICATIONS

This application claims the benefit and priority of application Ser. No. 60/116,007, filed Jan. 15, 1999, which is herein incorporated by reference for all purposes.

BACKGROUND OF THE INVENTION

This invention relates in general to a method of repositioning teeth for use in orthodontic treatment. Particularly, this invention relates to the use of orthodontic appliances for producing tooth movements. More particularly, this invention relates to the use of a plurality of elastic repositioning appliances for producing such tooth movements.

Orthodontic treatment is based on the principle that if prolonged pressure is applied to a tooth, tooth movement will occur as the bone around the tooth remodels. Bone is selectively removed in some areas and added in others. In essence, the tooth moves through the bone as it remodels, carrying its attachment apparatus with it as the socket of the tooth migrates. This attachment apparatus is a heavy collagenous supporting structure called the periodontal ligament (PDL) which attaches the tooth to the adjacent alveolar bone. The tooth remodeling is mediated by the PDL. Although the PDL is adapted to resist forces of short duration, prolonged force produces a different physiologic response, namely remodeling of the adjacent bone. Orthodontic tooth movement is made possible by the application of prolonged forces.

The simplest form of orthodontic movement is tipping. Tipping movements are produced when a single force is applied against the crown of a tooth. When this is done, the tooth rotates around its "center of resistance", a point at which resistance to movement can be concentrated for mathematical analysis. The center of resistance for a tooth is at the approximate midpoint of the embedded portion of the root, about halfway down the root. When the tooth rotates in this fashion, the PDL is compressed near the root apex on the same side as the force and at the crest of the alveolar bone on the opposite side. These areas account for only one-half the PDL area that could actually be loaded. Therefore, pressure in the two areas where it is concentrated is high in relation to the force applied to the crown. For this reason, forces used to tip teeth may be quite low and such movement may be easily achieved.

In many cases, mere tipping of the teeth is insufficient in completing orthodontic treatment. Translation, bodily movement of the tooth where the root apex and crown move in the same direction by the same amount, is often necessary. This may be accomplished by applying forces to the crown which create counterbalancing moments. Thus, the tooth would remain upright and move bodily. In this case, the total PDL area is loaded uniformly. Therefore, it is apparent that to produce the same pressure in the PDL and the same biologic response, twice as much force would be required for bodily movement as for tipping. To move a tooth so that it is partially tipped and partially translated would require forces intermediate between those needed for pure tipping and pure bodily movement.

For a number of reasons, including lowering the level of force applied to the teeth, at least part of the translation process is often accomplished by "tipping" and "uprighting." This technique is often referred to as the Begg approach or technique. Raymond Begg adapted current technology in the 1920's to produce the Begg appliance. The Begg appliance uses "stationary anchorage", in which movement teeth are allowed to tip while anchor teeth are allowed to only move bodily if at all. In the case of closing a premolar extraction site, anterior teeth would first be tipped distally. As a second step, the tipped teeth would be uprighted, moving the canine roots distally and torquing the incisor roots lingually. Using this technique, the optimum pressure for the anterior segment would be produced by about half as much force as if the anterior teeth were to be retracted bodily.

The Begg appliance and appliances using the Begg technique are typically bonded to the teeth. Bonding facilitates tooth movements by providing consistent points of purchase on the tooth for manipulation. During tipping, the crown is tipped in the direction of tooth movement. Interconnected bonded brackets or bands prevent the crown from substantially intruding the gingival line. The bonded appliances are then utilized to upright the tooth at its destination. However, many removable appliances, such as elastic repositioning appliances, do not have the benefit of bonding to manipulate the teeth. In these cases, teeth are commonly repositioned by manipulation of the crown directly. Points of purchase may be increased with the use of attachment devices on the crown. However, as a tooth becomes intruded during tipping, the portion of exposed surface area on the crown decreases. This diminishes the ability of an appliance, such as an elastic repositioning appliance, to "grab" onto a tooth for further manipulation. Therefore, the ability of accomplishing long, complicated movements in later stages of orthodontic treatment may be hindered. Further, translation of the tooth in the crown-first position is more difficult with the use of elastic repositioning appliances due to the slope of the crown. Force applied to the crown may serve to further intrude the tooth or may be reduced to a level of ineffectivity.

For these reasons, it would be desirable to provide alternative methods and systems for moving teeth. These methods should be compatible for use with any type of orthodontic appliance, both bonded and removably attachable. However, such methods may be particularly suitable for use with removable orthodontic appliances, including elastic repositioning appliances. In the case of elastic repositioning appliances, such methods and systems should also benefit the utilization of attachment devices, if available, and possibly lessen the need for additional attachment devices. At least some of these objectives will be met by the methods and systems of the present invention described hereinafter.

SUMMARY OF THE INVENTION

The present invention provides methods and systems of repositioning teeth for use in orthodontic treatment, with particular applicability to removable elastic repositioning appliances. Some traditional methods of repositioning teeth are most suitable for orthodontic appliances which are bonded to the teeth. Such bonding allows manipulation of the teeth which is not as easily affordable with removable appliances. Therefore, the present invention provides alternative repositioning movements which are particularly suited for removable elastic appliances.

Such appliances preferably comprise a polymeric shell having teeth-receiving cavities formed therein. The cavities generally conform to the patient's teeth, but certain cavities are slightly out of alignment with the initial tooth configuration. The appliance, however, is sufficiently resilient to accommodate or conform to the misaligned teeth, and will apply sufficient resilient force against such misaligned teeth in order to reposition the teeth to the desired position. Repetition of this process with successive appliances comprising new configurations eventually moves the teeth through a series of intermediate configurations to a final desired configuration. A full description of an exemplary elastic polymeric positioning appliance is described in U.S. Pat. No. 5,975,893, and in published PCT application WO 98/58596 which designates the United States and which is assigned to the assignee of the present invention. Both documents are incorporated by reference for all purposes.

Repositioning of teeth in orthodontic treatment typically involves a number of individual tooth movements, including but not limited to tipping, translation, root uprighting, rotation, extrusion and intrusion. Such movements are coordinated to reposition teeth anywhere within a gingival plane. A gingival plane may be defined as a plane formed by the arch of the gingival line. Often, tooth movements, such as translations, are described as occurring along the gingival line. This typically corresponds to mesial-distal movements. However, many labial-lingual movements are also required in orthodontics and occur in a direction substantially perpendicular to the gingival line. Likewise similar movements may be required along lines between these two axes. Therefore, a gingival plane may be defined to incorporate all of these lines or axes along which movement may take place.

In the methods of the present invention, a series of tooth movements are provided for moving a tooth from a first location to a desired location within a gingival plane. The movements may be grouped into three phases: 1) determining that the tooth is positioned so that its longitudinal axis is angled, having the axis portion passing through the root closer to the desired location than the axis portion passing through the crown, 2) translating the tooth toward the desired location with the axis portion passing through the root leading, and 3) positioning the tooth so that the longitudinal axis is substantially perpendicular to the gingival plane at the desired location.

In a first aspect of the methods of the present invention, the first phase of movements may involve a series of individual simultaneous or coordinated movements. In a preferred embodiment, the series may include three such movements: 1) rotation of the tooth around its center of rotation so that its longitudinal axis is angled less than 90 degrees from the gingival plane, 2) translation of the tooth toward the desired location, and 3) extrusion of the tooth so that the crown is not substantially intruded. Such movements are particularly applicable for achievement with an elastic repositioning appliance. Rotational forces applied to the crown of a tooth by an elastic appliance inherently apply simultaneous translational and extrusional forces. For example, rotational forces applied to the crown in the mesial direction will result in translation in the distal direction and extrusion, in addition to rotation. Therefore, it is desired to rotate the tooth so that the portion of the longitudinal axis passing through the root is closer to the desired location than portion passing through the crown, i.e. root-first. However, the tooth may be presented in this position and repositioning may begin with the second phase.

In a second aspect of the methods of the present invention, the second phase of movements involves translating the tooth toward the desired location with the axis portion passing through the root leading. Translation of the tooth in this orientation provides usable points of purchase on the crown through which an elastic positioning appliance may transmit translational forces of sufficient level and control.

In a third aspect of the methods of the present invention, the third phase of movements involves a series of individual simultaneous or coordinated movements. In a preferred embodiment, the series may include three movements: 1) rotation of the tooth around its center of rotation so that its longitudinal axis is angled less than 90 degrees from the gingival plane, 2) translation of the tooth toward the desired location, and 3) intrusion of the tooth so that the crown is not substantially intruded. As in the first phase, such movements are particularly applicable for achievement with an elastic repositioning appliance. When rotational forces are applied to the crown of a root-first tooth by an elastic appliance in the opposite direction as Phase 1, the appliance inherently applies simultaneous translational and intrusional forces. For example, rotational forces applied to the crown in the distal direction will result in translation in the distal direction and intrusion, in addition to rotation. Therefore, such movements will position the tooth at the desired location with the longitudinal axis substantially perpendicular to the gingival plane.

In a fourth aspect, the systems and methods of the present invention involve the use of one or more attachment devices positioned on the teeth for use in transmitting forces from the elastic positioning adjustment appliance to the teeth. The attachment devices may be of simple construction, having an attachment body and a base. The base is typically bonded to the tooth with the body protruding therefrom. This affords an additional point of purchase on the tooth for added leverage and control. When the elastic appliance is positioned on the teeth, the appliance may apply force to the attachment devices for transmission to the underlying teeth. Thus, the attachment devices may be utilized in implementing the above described repositioning movements. A full description of exemplary attachment devices is described. Co-pending application Ser. No. 09/454,786, assigned to the assignee of the present invention, incorporated by reference for all purposes.

In a fifth aspect, the methods of the present invention may be used with more conventional orthodontic devices, such as brackets to the teeth. In these cases, the above described movements may be translated to the bonded bracket by the use of wires, elastic bands or similar devices. Likewise, such forces may be transmitted from an appliance to an attachment device with similar wire, elastic bands or devices.

A further understanding of the nature and advantages of the invention will become apparent by reference to the remaining portions of the specification and drawings.

BRIEF DESCRIPTION OF THE DRAWINGS

FIGS. 5A–D show the individual steps of the movements of Phase 1.

FIGS. 10A–D are simplified depictions of force applications on a tooth by one or a series of elastic repositioning appliances.

FIGS. 12A–D are a schematic illustration of the possible utilization of attachment devices to apply basic forces to the teeth.

FIG. 13 is an illustration of a possible impression orientation to achieve simultaneous movements.

DESCRIPTION OF THE SPECIFIC EMBODIMENTS

As described previously, the methods of the present invention may be utilized to reposition teeth within a gingival plane. A gingival plane may be defined as a plane formed by the arch of the gingival line. However, for illustration purposes, the systems and methods of the present invention will be described according to movements along a gingival line. It may be appreciated that the scope of the invention is not limited to movement along such a gingival line.

Figure 1:
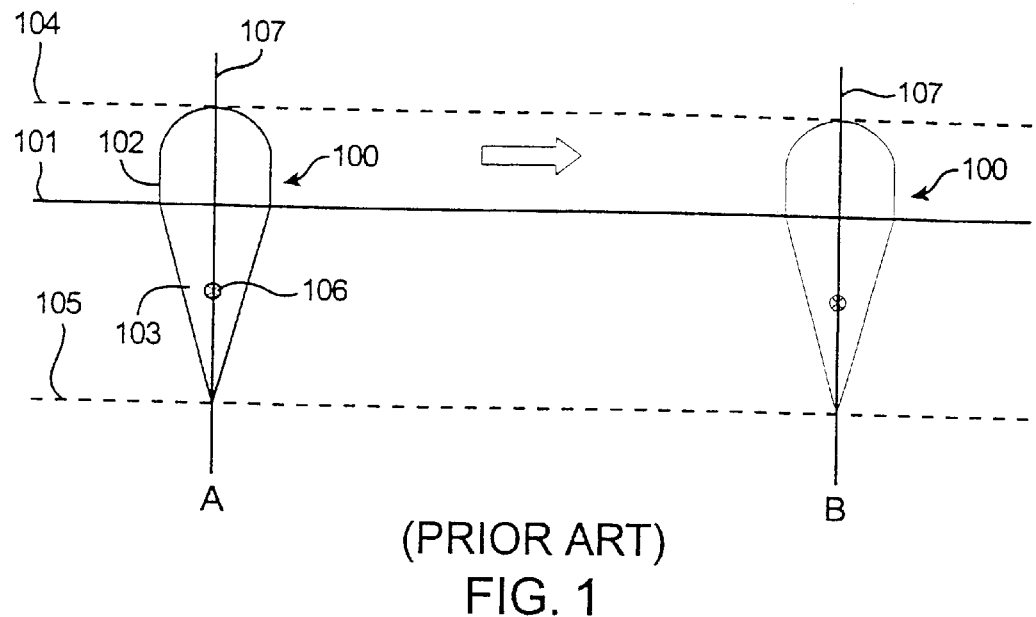
FIG. 1 is a schematic representation of sample first location and desired location along the gingival line.

Referring to FIG. 1, a tooth 100 may be repositioned from location A to location B along a gingival line 101. The tooth 100 is depicted as having a crown 102 substantially above the gingival line 101 and a root 103 substantially below the gingival line 101. A dashed line 104 is shown tangent to the crown 102 to serve as a guideline during repositioning. Similarly, a dashed line 105 perpendicular to the root is also shown for guideline purposes. A center of resistance 106 is located at the approximate midpoint of the embedded portion of the root, about halfway between the root apex and the crest of the alveolar bone. This is the point at which resistance to movement may be concentrated for mathematical analysis. Passing through the crown 102, root 103 and center of resistance 106 is a longitudinal axis 107. In this example, the tooth 100 will be repositioned from an upright position at location A to an upright position at location B, therefore the longitudinal axis 107 is perpendicular to the gingival line 101 in both locations.

Figure 2:
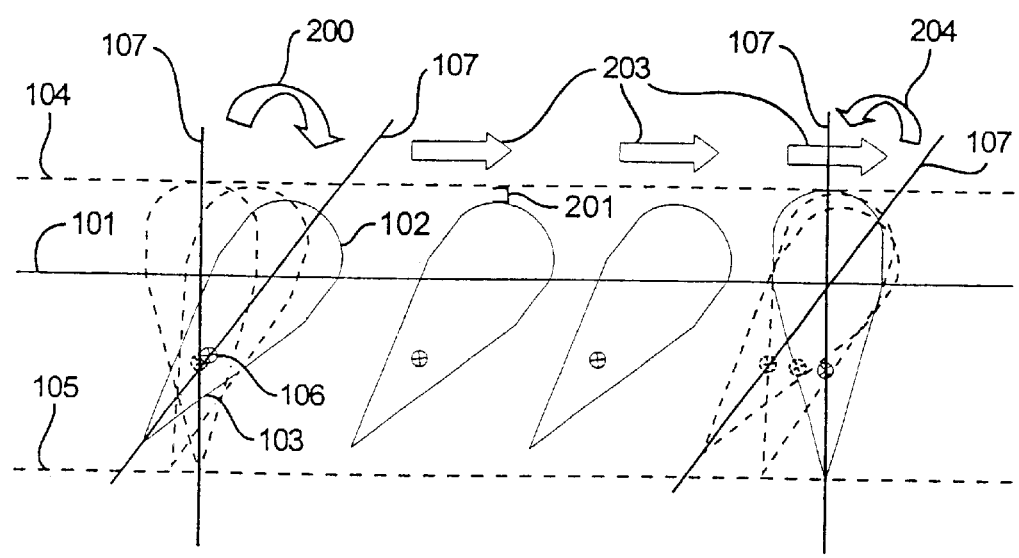
FIG. 2 is a schematic depiction of a series of prior art tooth repositioning movements to reposition a tooth from the sample first location to the desired location along the gingival line.

The tooth 100 may be bodily translated from location A to location B by moving the crown 102 and the root 103 in the same direction by the same amount. Typically, this may require 70–120 gm of force. However, as previously described, the same translation may be alternatively accomplished with lower overall force by involving "tipping" and "uprighting" movements, as shown in FIG. 2. If a single force is applied to the crown 102 of the tooth 100, the tooth 100 will not only translate but also rotate around the center of resistance 106, because a moment is created by applying a force at a distance from the center of resistance 106. Such rotation is depicted by a clockwise arrow 200 and requires approximately 35–60 gm of force in its pure form. In this example, the center of resistance is the center of rotation. However, if a force and a couple are strategically applied to an object, the center of rotation can be controlled and made to have any desired location. Therefore, hereinafter, rotations will be described as occurring around a center of rotation, which may or may not be the center of resistance.

As shown in FIG. 2, the tooth 100 is usually tipped so that the portion of the longitudinal axis 107 passing through the crown 102 is closer to the desired location, location B, than the axis 107 portion passing through the root 103, i.e. the tooth is angled "crown-first" in the movement direction. Such tipping causes intrusion of the crown 102, reducing the surface area located above the gingival line 101. This can be seen by the gap between the dashed line 104 and the crown 102 demarcated by bracket 201. For repositioning over relatively large expanses, some translation may occur with the tooth 100 in this position, as depicted by horizontal arrows 203. As the tooth 100 approaches location B, the tooth 100 may then be "uprighted" to its final position. Uprighting involves movement including rotation to draw the root 103 back up under the crown 102 so that the longitudinal axis 107 is substantially perpendicular to the gingival line 101. This is depicted by counterclockwise arrow 204 and requires approximately 50–100 gm of force in its pure form.

The above described repositioning movements are satisfactory for use with orthodontic devices which are largely bonded to the teeth. Such bonding implements manipulation of the teeth which have become intruded during movements such as tipping. However, orthodontic devices which do not utilize or rely on bonding to the teeth for long or complicated repositioning movements may be hindered by consequential intrusion or other effects which may decrease the available points of purchase on a tooth.

For example, one type of orthodontic appliance which does not utilize bonding to the teeth is a removable elastic repositioning appliance. Such elastic positioners comprise a thin shell of polymeric material having a cavities shaped to receive and resiliently reposition the teeth from one tooth arrangement to a successive tooth arrangement. The shell generally conforms to the patient's teeth but is slightly out of alignment with the initial tooth configuration. The misalignment creates forces on the teeth to reposition the teeth into the successive tooth arrangement. To achieve forces capable of producing such movements, the appliance must be relatively stiff in appropriate areas to both anchor the appliance on the teeth and apply force to designated tooth surfaces. Anchoring and force application are dependent on the surface characteristics of the teeth, particularly in the crown region. Therefore, any intrusion of a crown reduces the available surface area and possibly critical surface features for manipulation. This may hinder future manipulations of the tooth and other teeth which may rely on the tooth for anchoring or other functions.

Figure 3:
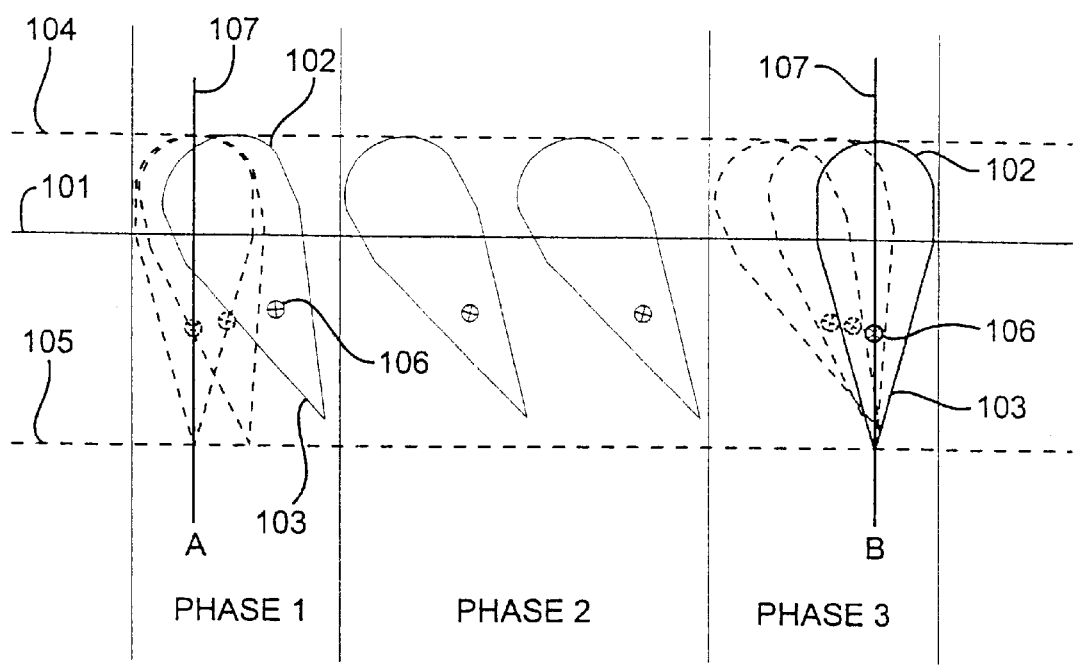
FIG. 3 is a schematic view of the series of tooth repositioning movements of the present invention to reposition a tooth from the sample first location to the desired location in three phases, Phase 1, Phase 2 and Phase 3.
Figure 4:
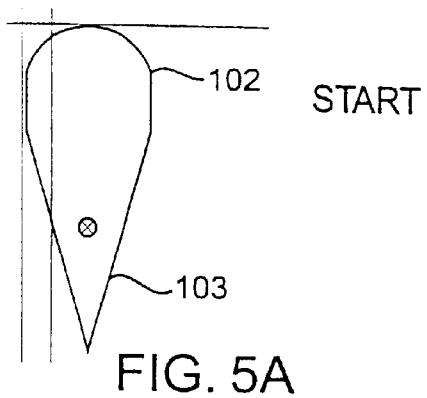
FIG. 4 is a schematic view of the movements of Phase 1.
Figure 4:
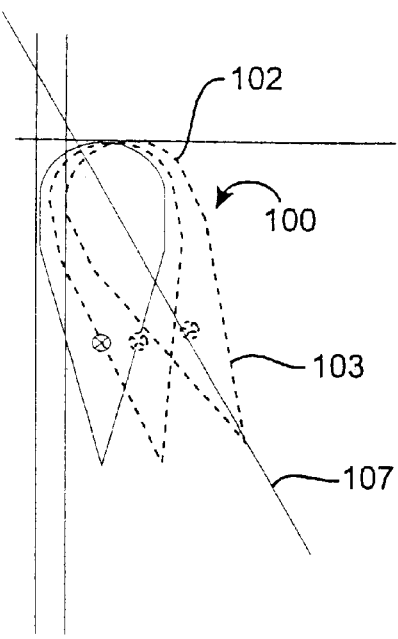
Figure 5B:
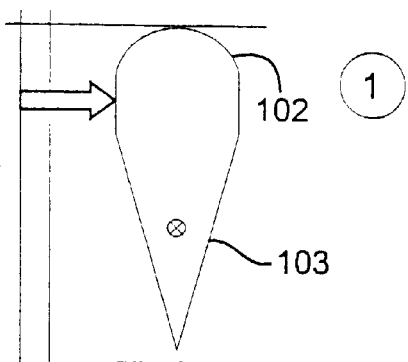
Figure 5C:
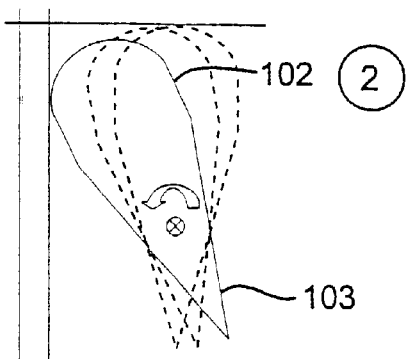
Figure 5D:
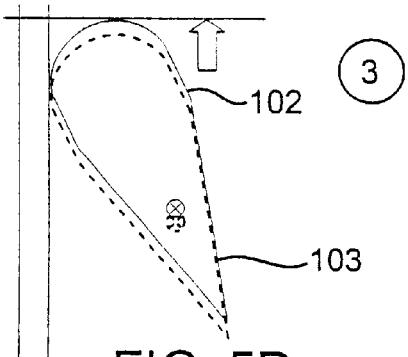

The systems and methods of the present invention maximize the availability of tooth surfaces and total surface area during repositioning, enabling longer and more complicated tooth movements. Referring to FIG. 3, a preferred embodiment of a series of tooth movements provided by the present invention is depicted for moving a tooth 100 from location A to location B. The movements may be grouped into three phases as shown. Referring to FIG. 4, Phase 1 involves angling the tooth 100 "root-first" so that the portion of the longitudinal axis 107 passing through the root 103 is closer to the desired location, location B, than the axis 107 portion passing through the crown 102. Such angling may be a combination of three basic repositioning movements undertaken simultaneously. FIGS. 5A–D, reveal possible simultaneous motions involved in Phase 1. The tooth 100 begins in location A, as depicted in FIG. 5A. The tooth 100 may then be simultaneously translated, FIG. 5B, rotated, FIG. 5C, and extruded, FIG. 5D. It may be appreciated that such movements may not all be simultaneous or such movements may be undertaken in an alternative coordinated pattern. Similarly, not all movements may be included or additional movements may be incorporated. However, in all cases the tooth will be positioned in a "root-first" orientation with sufficient crown exposure to facilitate movement with a removable elastic repositioning appliance. If the tooth is already in such a position, the sequence of movements may begin at Phase 2.

Figure 6:
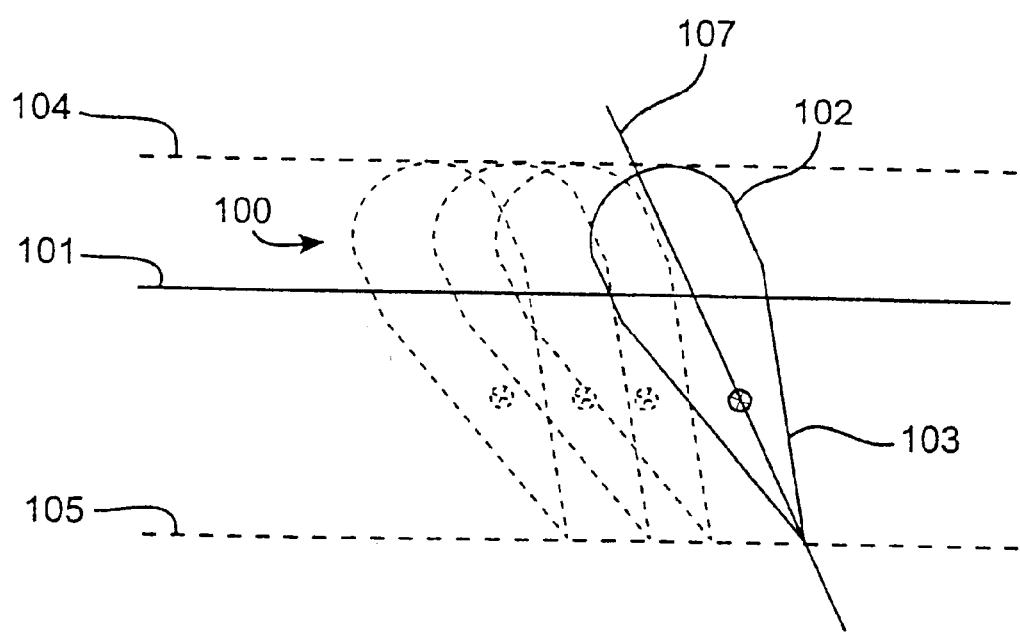
FIG. 6 is a schematic representation of "root-first" translation of a tooth in Phase 2.

Phase 2 may be a simple translation of the tooth 100 in the angled position, as shown in FIG. 6. Such translation is "root-first" in that the portion of the longitudinal axis 107 passing through the root 103 is closer to the desired location than the portion of the axis 107 passing through the crown 102. Thus, the tooth may be described as moving with the root leading. Of particular interest is that the crown 102 is tangent to the dashed line 104 throughout the movement; the gap shown in FIG. 3 is no longer present. This is a simple way of showing that more of the crown is exposed and available for manipulation than with traditional repositioning methods illustrated in FIG. 3. Thus, it may be appreciated that it is not a requirement of the present invention to perform the movements so that the crown 102 is continuously tangent to the dashed line 104. Such consistency is present for illustrative purposes.

Figure 8A:
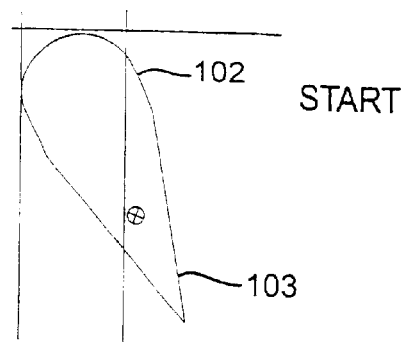
FIGS. 8A–D show the individual steps of the movements of Phase 3.
Figure 7:
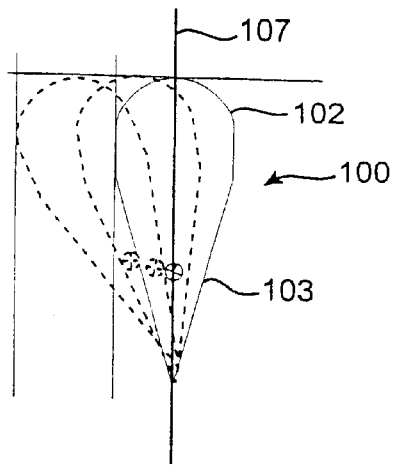
FIG. 7 is a schematic view of the movements of Phase 3.
Figure 8B:
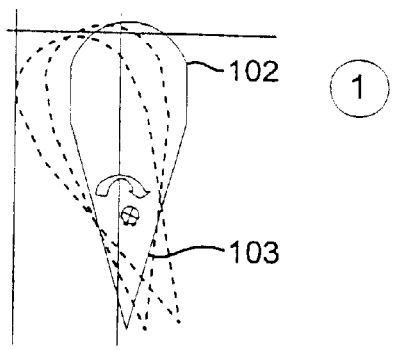
Figure 8C:
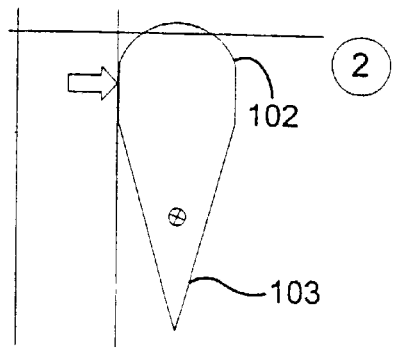
Figure 8D:
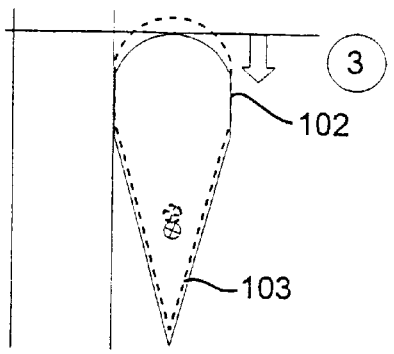

The tooth 100 may be repositioned at the desired location, location B, by straightening the tooth 100 to its upright position as seen in Phase 3, FIG. 7. Phase 3 involves straightening the tooth 100 so that the longitudinal axis 107 is more perpendicular to the gingival line 101. Such straightening may be a combination of three basic repositioning movements undertaken simultaneously. FIGS. 8A–D reveal possible simultaneous motions. The tooth 100 begins in an intermediate angled positioned, as depicted in FIG. 8A. The tooth 100 may then be simultaneously rotated, FIG. 8B, translated, FIG. 8C, and intruded, FIG. 8D. Again, it may be appreciated that such movements may not be simultaneous or such movements may be undertaken in an alternative coordinated pattern. Similarly, not all movements may be included or additional movements may be incorporated.

Figure 9:
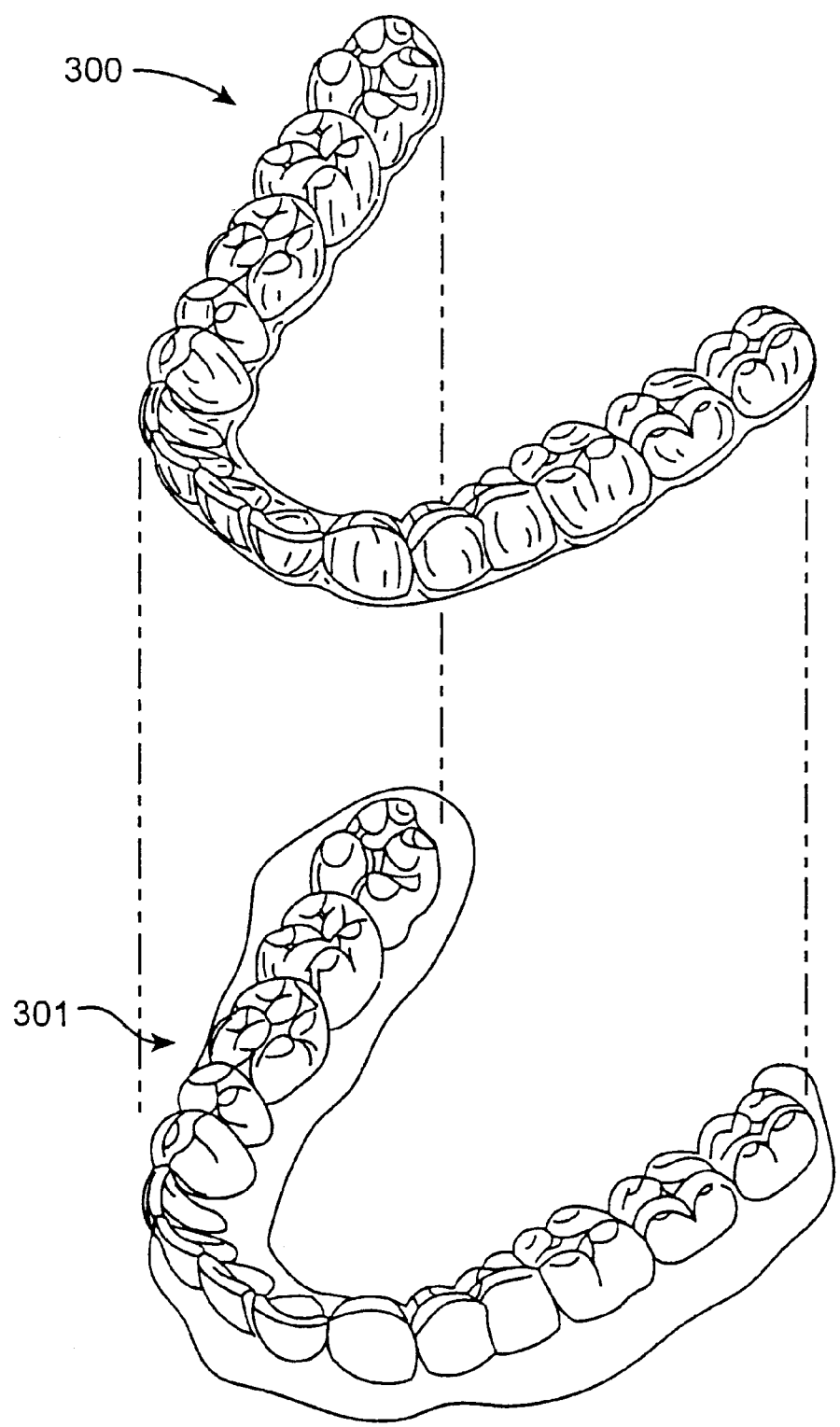
FIG. 9 is a perspective view of an exemplary elastic repositioning appliance.

Repositioning teeth as described above may be achieved with the use of a number of orthodontic devices and appliances. Such repositioning movements are particularly suitable for removable elastic repositioning appliances. As shown in FIG. 9, an elastic appliance 300 will preferably, but not necessarily, fit over all teeth present in the upper or lower jaw 301. A system of elastic appliances may be comprised of a plurality of such appliances intended to be worn by a patient successively in order to achieve the gradual tooth repositioning described hereinbefore. Each appliance may be formed to apply force on designated tooth surfaces to achieve a desired tooth movement, such as translation, rotation, extrusion or intrusion. Simplified depictions of such force applications by one or a series of appliances may be seen in FIGS. 10A–D. Referring to FIG. 10A, translational force 400 may be applied by a slight horizontal misfit of the appliance 300 to the tooth 100. Rotational force 401 may be applied by a slight rotational misfit of the appliance 300 to the tooth 100, FIG. 10B. As seen in FIG. 10C, extrusional force 404 may be applied with the use of undercuts 405 in the appliance 300 to assist in "grabbing" and extruding the tooth 100. FIG. 10D illustrates intrusional force 406 in which the appliance 300 is slightly vertically misfit in relation to the tooth 100. Such intrusional forces often require the use of an attachment device, as will be described.

Figure 11A:
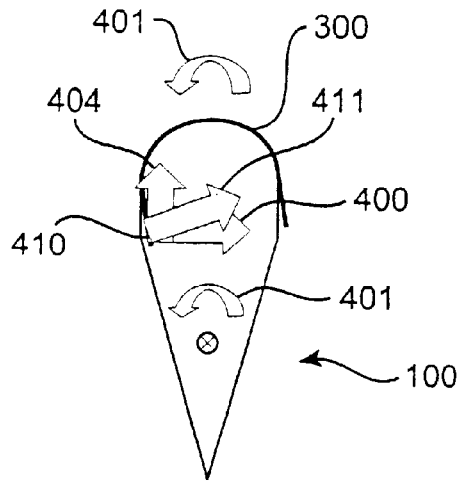
FIGS. 11A–C are a schematic illustration the inherent advantages of elastic repositioning appliances in implementing the methods of the present invention.
Figure 11B:
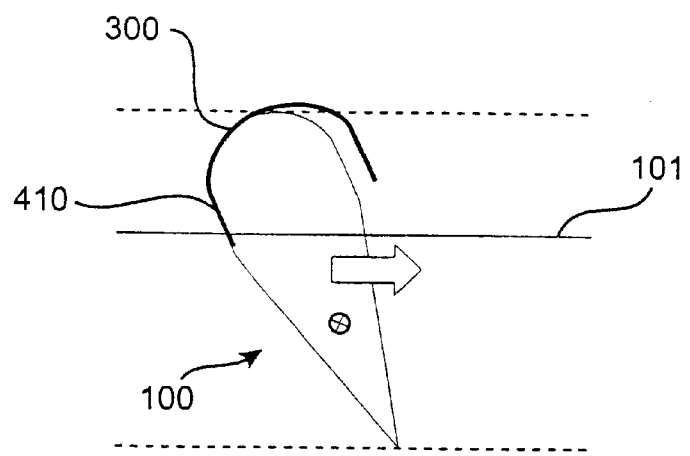
Figure 11C:
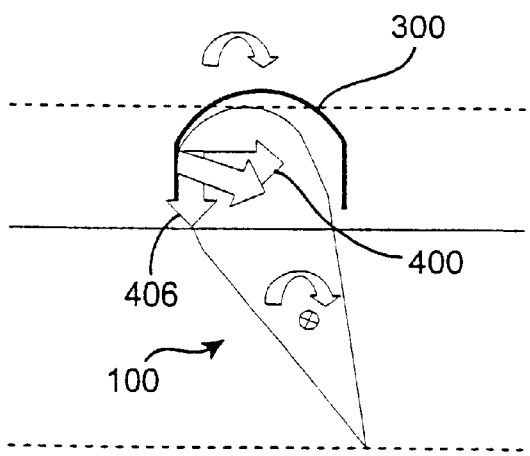

The application of force by an elastic repositioning appliance provides specific advantages in the "root-first" series of movements. Referring to FIG. 11A, when an appliance 300 is misfit to apply a rotational force 401 to a tooth 100, the lower edge 410 of the appliance 300 applies a diagonal force vector 411 on the intruding side of the rotating tooth 100. The diagonal force vector 411 represents the vector sum of two forces along perpendicular axes, a translational force 400 and an extrusional force 404. Therefore, rotation with such an appliance 300 will simultaneously apply translational force 400 and extrusional force 404. This action is of most benefit to movements in the "root-first" orientation as such translation will then be in the appropriate direction. Likewise, further translation by force of the appliance 300 is most easily accomplished by "pushing" the tooth 100 with the use of the lower edge 410, as seen in FIG. 11B. The lower edge 410 serves as an undercut which aids in "grabbing" the tooth 100 for manipulation. Direct contact of the appliance 300 with the tooth 100 at this location allows direct controlled transmission of force, as if "pushing". This would not be the case if the tooth were oriented in a "crown-first" position, as the undercut would be on the misfit, receiving side of the appliance 300. And finally, straightening of the tooth 100 at the desired location would similarly be benefited by use of an elastic positioning appliance 300. As illustrated in FIG. 11C, rotation with such an appliance 300 will simultaneously apply translational force 400 and intrusional force 406. Therefore, the systems and methods of the present invention are of significant applicability to use with elastic repositioning appliances.

In some cases of intrusion and other required force applications throughout orthodontic treatment, the native tooth surfaces may still be inadequate to provide sufficient anchoring or to impart sufficient force on the teeth to be repositioned. To overcome these limitations, the present invention may involve the use of one or more attachment devices which may be bonded to preselected attachment points on the teeth or dental features to provide the appropriate physical leverage. The attachment devices may have a very simple construction, in some instances being only a bump, bead, wedge, or other body or structure. The attachment devices may typically protrude up to 2.5 mm from the surface of the tooth. When the elastic appliance is positioned on the teeth, the appliance may apply force to the attachment devices for transmission to the underlying teeth.

FIGS. 12A–D schematically illustrate the possible utilization of attachment devices to apply basic forces to teeth. As seen in FIG. 12A, an attachment device 500, depicted by a solid grey rectangle, may be bonded to the crown 102 of a tooth 100. A corresponding impression 501, depicted by a rectangular outline, of the attachment device 500 in the wall of the elastic repositioning appliance 300 may be horizontally misfit. Such misfitting may apply a translational force 400 to the attachment device 500, and therefore to the underlying tooth 100. Similarly, an impression 501 may be rotationally misfit, as in FIG. 12B, to apply a rotational force 401 to an attachment device 500 and underlying tooth 100. And, as shown in FIGS. 12C and 12D, an impression 501 may be vertically misfit higher or lower than the attachment device 500 to impart an extrusive force 404 or intrusive force 406 respectively. Thus, combination movements undertaken simultaneously may be achieved by combining impression 501 orientations for the desired result. For example, FIG. 13 illustrates a possible impression 501 orientation to achieve simultaneous rotation and extrusion. Slight rotational and vertical misfitting of the impression 501 to the attachment device 500 may impart simultaneous rotational force 401 and extrusive force 404.

Figure 14A:
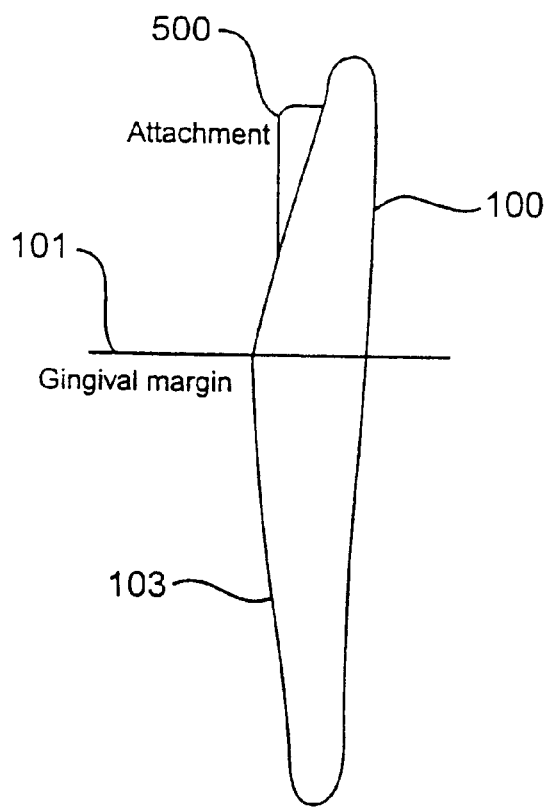
FIGS. 14A–E are side views of teeth with various attachment devices for use with elastic repositioning appliances in implementing the methods of the present invention.
Figure 14B:
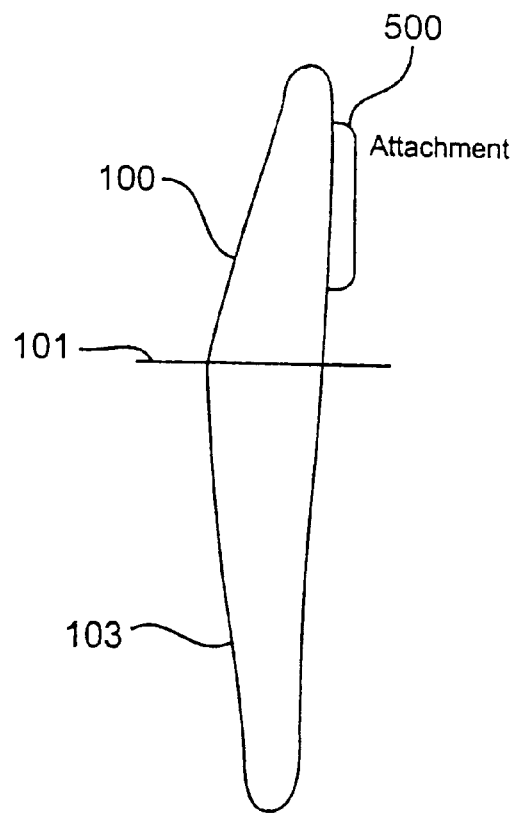
Figure 14C:
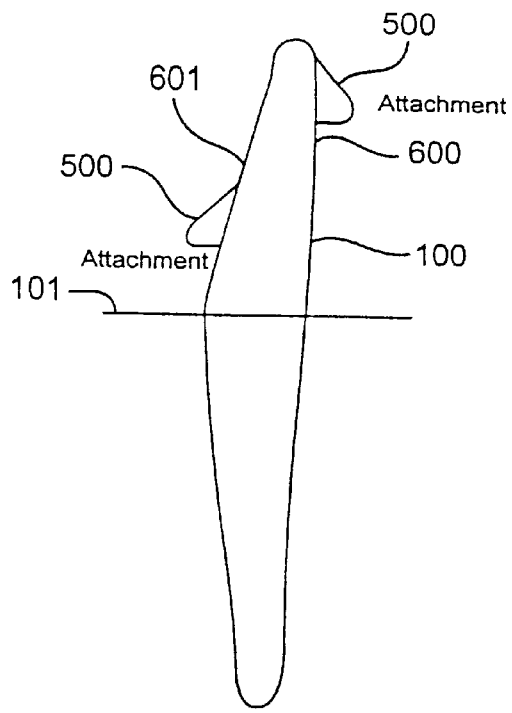
Figure 14D:
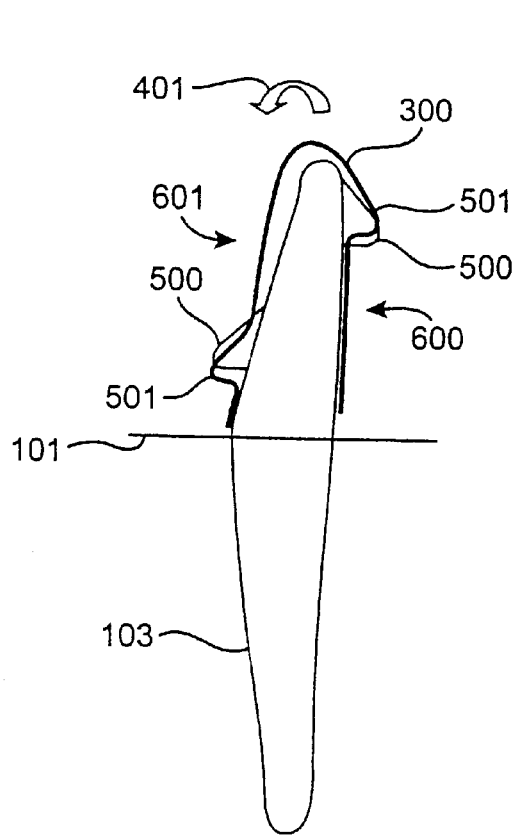
Figure 14E:
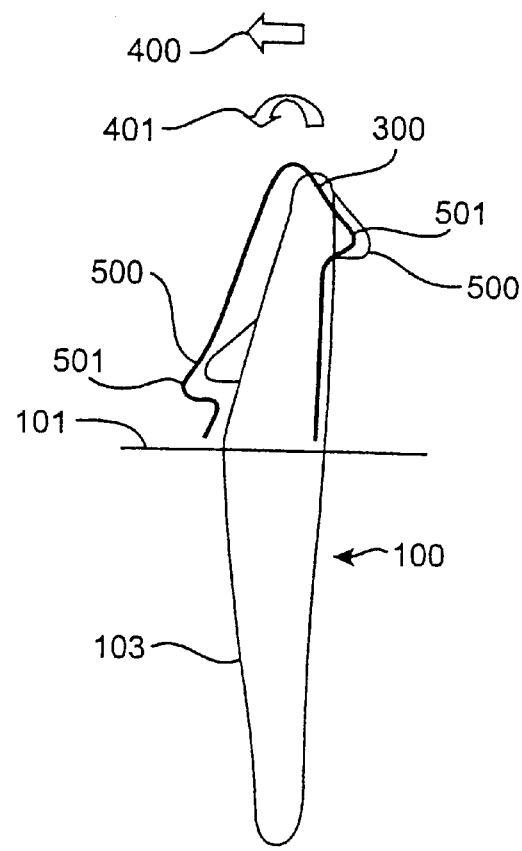

As illustrated in FIGS. 14A and 14B, the attachment devices 500 may be of a variety of geometries and may be placed in any location on the tooth 100 surface so long as the devices 500 provide adequate points of purchase. In some cases, a pair of attachment devices 500 may be positioned on a single tooth 100 to impart a single repositioning movement. For example, as shown in FIG. 14C, attachment devices 500 may be positioned on either side of an incisor, one on the buccal side 600 near the crown 102 tip and one on the lingual side 601 near the gingival line 101. As seen in FIG. 14D, an elastic repositioning appliance 300 may be formed to so that corresponding impressions 501 in the appliance 300 wall vertically misfit both of the attachment devices 500 when in place. The impression 501 on the buccal side 600 may be misfit higher than the corresponding attachment device 500 and the impressions 501 on the lingual side 601 may be misfit lower than the corresponding attachment device 500. The result is a rotational force 401 in the lingual direction. Likewise, a combination of rotational force 401 and translational force 400 may be achieved by misfitting both the attachment devices 500 and the tooth 100 itself, as depicted in FIG. 14E.

Figure 15:
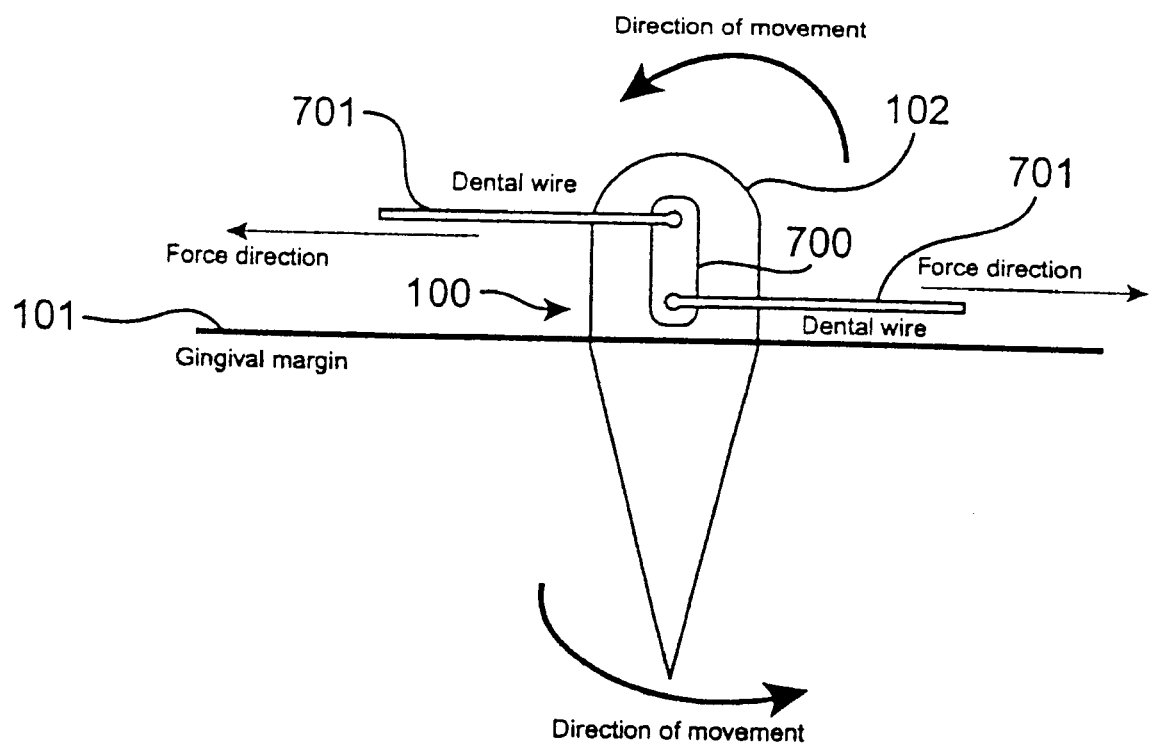
FIG. 15 is a schematic representation of applying the methods of the present invention to a tooth with the use of conventional orthodontic devices.

As described, the systems and methods of the present invention typically involve a plurality of incremental position adjustment appliances 300 to produce the repositioning movements over prolonged periods of time. Thus, each appliance 300 may be formed to strategically misfit one or more teeth 100 and/or attachment devices 500 to impart specific anchoring or repositioning forces on the underlying teeth 100. Used in progression, a series of movements as described above may be achieved. Alternatively, such movements may be achieved with more conventional orthodontic devices, such as brackets bonded to the teeth. Referring to FIG. 15, a bracket 700 may be bonded to the crown 102 of a tooth 100. Dental wires 701 may be attached to opposite ends of the bracket 700 to which force may be applied. Such opposing forces may rotate the tooth 100 in a desired orientation. Thus, the dental wires 701 may be part of an orthodontic treatment plan involving conventional braces. It may be appreciated that the bracket 700 may be termed an attachment device 500 and may be used in conjunction with removable appliances such an elastic repositioning appliance 300. In this case, the wires 701 may be linked to the appliance 300, or may be in the form of elastic bands or the like linked in a similar fashion.

What is claimed is:

1. A method of repositioning a tooth from a first location to a second location along a gingival plane comprising:

choosing at least one tooth, having a root, a crown, a center of rotation and a longitudinal axis passing through the root, the crown and the center of rotation;

rotating the tooth so that the crown leans away from the desired location; and translating the tooth toward the desired location with the crown leaning away from the desired location.

2. The method of claim 1, further comprising at least partially extruding the tooth prior to translating the tooth.

3. The method of claim 1, further comprising rotating the tooth around the center of rotation so the longitudinal axis is substantially perpendicular to the gingival plane after the tooth has been translated to the desired location.

4. The method of claim 3, further comprising at least partially intruding the tooth after the tooth has been translated to the desired location.

5. The met hod of claim 1, wherein rotating and translating comprise the successive of use of elastic repositioning appliances having different geometries.

6. A system for repositioning teeth from an initial tooth arrangement to a desired tooth arrangement, said system comprising:

a plurality of dental position adjustment appliances having a polymeric shell with cavities shaped to receive and resiliently reposition teeth, including at least one appliance which is shaped to rotate a preselected tooth so that a crown of the tooth leans away from a desired location and at least another appliance shaped to apply a force to the at least one tooth to translate the at least one tooth toward the desired location.

7. The system of claim 6, further comprising at least a third appliance which is shaped to rotate the crown of the at least one tooth upwardly after the tooth has been moved to the desired location.

8. The system of claim 7, wherein the plurality of dental position appliances further includes at least one appliance with cavities shaped to apply force to at least partially extrude the tooth prior to or during rotation of the tooth or movement of the tooth toward the desired location with the root leading.

9. The system of claim 7, wherein the plurality of dental position appliances further includes at least one appliance with cavities shaped to apply force to at least partially intrude the tooth during or subsequent to rotation of the tooth to its upright position.

10. A system for repositioning teeth from an initial arrangement to a desired tooth arrangement, said system comprising:

a plurality of dental position adjustment appliances having a polymeric shell with cavities shaped to receive and resiliently reposition teeth, including at least one appliance which is shaped to rotate a preselected tooth so that a crown of the tooth leans away from a desired location and at least another appliance shaped to apply a force to the at least one tooth to translate the at least one tooth toward the desired location; and one or more attachment devices positionable on the teeth for use in transmitting forces from the positioning adjustment appliances to the teeth.

11. The system of claim 10, further comprising at least a third appliance which is shaped to rotate the crown of the at least one tooth upwardly after the tooth has been moved to the desired location.

12. The system of claim 11, wherein the plurality of dental position adjustment appliances further includes at least one appliance with cavities shaped to apply force to the attachment device(s) on at least one tooth to at least partially extrude the tooth prior to or during rotation of the tooth to angle the longitudinal axis or movement of the tooth toward the desired location with the root leading.

13. The system of claim 10, wherein the attachment device(s) are used to transmit forces from the dental positioning appliances to the tooth for movement of the tooth toward a desired location with the root leading in the direction of the desired location.

14. The system of claim 10, wherein the plurality of dental position adjustment appliances includes at least one appliance with cavities shaped to apply force to the attachment device(s) on at least one tooth to rotate the tooth a round its center of rotation so that it is in its upright position, during or subsequent to movement of the tooth toward the desired location with the root leading in the direction of the desired location.

15. The system of claim 14, wherein the plurality of dental position adjustment appliances includes at least one appliance with cavities shaped to apply force to the attachment device(s) on at least one tooth to at least partially intrude the tooth during or subsequent to rotation of the tooth to its upright position or movement of the tooth toward the desired location with the root leading.

* * * * *